United States Patent [19]

Holtkamp, Sr.

[11] Patent Number: Plant 6,479

[45] Date of Patent: Dec. 20, 1988

[54] AFRICAN VIOLET PLANT NAMED ROXANNA

[76] Inventor: Reinhold Holtkamp, Sr., Werther Strasse 112, D4294 Isselburg, Fed. Rep. of Germany

[21] Appl. No.: 21,789

[22] Filed: Mar. 4, 1987

[51] Int. Cl.[4] ..... A01H 5/00

[52] U.S. Cl. ..... Plt./69

[58] Field of Search ..... Plt./69

*Primary Examiner*—James R. Feyrer

*Attorney, Agent, or Firm*—Schwartz, Jeffery, Schwaab, Mack, Blumenthal & Evans

[57] ABSTRACT

A new and distinct cultivar of African violet named Roxanna, characterized by its single mainly white flowers with red-purple centers and edges with additional petals occasionally appearing in the center; strong, upright flower stems that curve toward the center to form a bouquet above the leaves; profuse flowering; vigorous growth habit, flowering 8–10 weeks after potting, and its long-lasting and non-dropping flowers.

1 Drawing Sheet

The present invention comprises a new and distinct cultivar of African violet plant, botanically known as *Saintpaulia ionantha,* and hereinafter referred to by the cultivar name Roxanna.

The new cultivar was referred to during the breeding and selection process by the designation G 17/23, and is a product of a planned breeding program. The new cultivar was originated from a cross made by me in the controlled breeding program in Isselburg, Federal Republic of Germany. The female, or seed parent, was a cultivar designated D 150/4 White Red Girl. The male, or pollen parent, was a cultivar designated 3/78 Violet Purple.

Roxanna was discovered and selected by me in 1984 as a flowering plant within the progeny of the stated cross in a controlled environment in Isselburg, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Roxanna has not been observed under all possible environmental conditions. The phenotype may vary significantly with variations in environment such as temperature, light intensity and day length. The following observations, measurements and values describe the new cultivar as grown in Haffen, Federal Republic of Germany, and Nashville, Tenn., under greenhouse conditions which closely approximate those generally used in commercial practice.

The following traits have been repeatedly observed and are determined to be basic characteristics of Roxanna which in combination distinguish this African violet as a new and distinct cultivar:

(1) Strong, upright flower stems slightly curving toward the center.

(2) First flash of flowers form a tight bouquet above the leaves.

(3) Long blooming period.

(4) Profuse flowering on medium long stems (5.5–7 cm).

(5) Each plant carries up to 8–10 and more upright flower stems, each of which carries 7–9 flowers.

(6) Vigorous grower, compact habit.

(7) Plant saleable 9–10 weeks after potting.

(8) Medium dark, green velvety leaves, slightly hairy.

(9) Long-lasting, non-dropping flowers.

(10) Seed capsule pushes slightly through.

(11) After maturity the flowers dry off, and remain on the peduncle without being infected by botrytis.

(12) White purplish-red flower that has a dark center that bleaches out towards the margins. The edges of the petals are of the same color as the center.

(13) The flower has additional little petals appearing at the center of the flower, giving the flower a semi-double appearance.

The accompanying color photographic drawing shows a typical specimen plant of the new cultivar. The colors appearing in the photograph are as true as possible with color illustrations of this type.

In the following description, color references are made to The Royal Horticultural Society Colour Chart (RHS), except where general colors of ordinary significance are referred to. Color values were taken under natural sunlight at approximately 2:00 p.m. in Nashville, Tenn.

Botanical classification: *Saintpaulia ionantha,* Ramat., cv. Roxanna.

Parentage:

*Male parent.*—3/78 Violet purple.

*Female parent.*—D 150/4 White Red Girl.

Propagation: The new cultivar holds its distinguishing characteristics through successive propagations by leaf cuttings.

Plant: From 8 cm to 9 cm tall when grown in pots, and approximately 27–29 cm in diameter when fully grown.

*Leaves.*—General form: Heart shaped. Diameter: 60–70 mm. Texture: Leatherlike. Aspect: Velvet, slight hairy, smooth edges. Veins: Underside light green, shiny. Color (upper side): Yellow Green Group 147A. Color (under side): Yellow Green Group 148D. Petiole: Strong, wire-like, light green.

*Flowers.*—Buds: Bell-shaped, 7–9 mm before opening. Sepals: Spear-shaped, hairy. Color: Before opening, brownish green, medium green on mature flowers. Calyx: Shape: Funnel-shaped. Aspect: Spear-shaped, hairy. Peduncle: Character: Strong, upright, hairy. Color: Brownish. Individual flowers: Size: 40–45 mm. Shape: Most flowers are single, with heavily frilled edges. Some flowers have additional small petals in center which give the flower a semi-double appearance. Color (upper side): White with 74A-B at center and radiating from center to bleach in with white; slight but visible 74A-B on edges of petals. Color (under side): White with 77C. Borne: Each flower stem carries 4–7 and more flowers on strong, upright wire-like peduncles that produce compact flower heads above the leaves. Flowering Habit: Flowers 8–10 weeks after potting, with flowers being long-lasting and non-dropping.

*Reproductive organs.*—Stamens: 2. Anthers: 2 with two anther cells each. Filaments: 2–3 mm. Pollen color: Yellow 7A. Styles: 7 mm, dark purple with a light green base.

*Roots.*—Normally developed, white when young, turning slightly brownish when older.

Disease resistance: Good.

General observations: Roxanna is a very attractive plant having a compact flower head of white-purple flowers surrounded by medium to dark green, shiny leaves. The flower has a red-purple center that bleaches out towards the margins, and the edges of the petals are of the same color as the center. The individual flower is single, but frequently additional petals appear at the center, giving the flower a semi-double appearance. The leaf petiole is flexible when grown under natural light condition. After maturity, the flowers dry off, and remain on the peduncle without becoming infected by botrytis.

I claim:

1. A new and distinct cultivar of African violet named Roxanna, as described and illustrated, and particularly characterized by its single mainly white flowers with red-purple centers and edges with additional petals occasionally appearing in the center; strong, upright flower stems that curve toward the center to form a bouquet above the leaves; profuse flowering; vigorous growth habit, flowering 8–10 weeks after potting, and its long-lasting and non-dropping flowers.

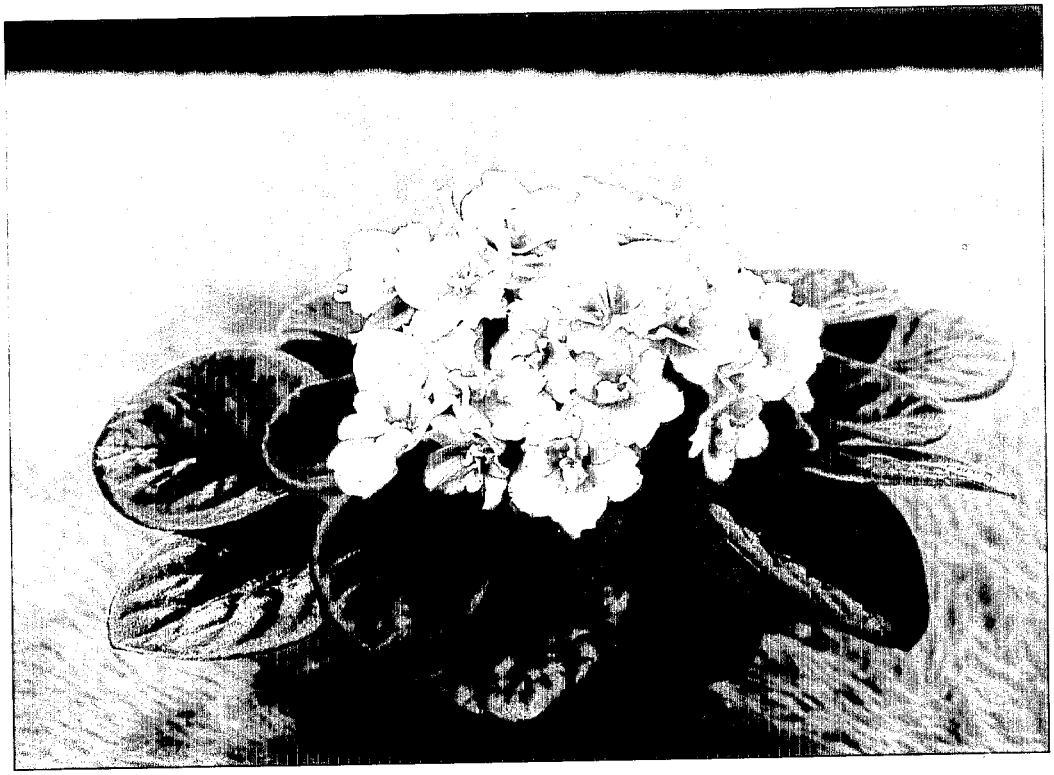

* * * * *